US00PP11835P2

(12) United States Plant Patent
Rother

(10) Patent No.: US PP11,835 P2
(45) Date of Patent: Apr. 3, 2001

(54) SUTERA PLANT NAMED 'LAVENDER STORM'

(76) Inventor: Reinhard W. Rother, P.B. 327, Emerald, Victoria (AU)

( * ) Notice: Subject to any disclaimer, the term of this patent is extended or adjusted under 35 U.S.C. 154(b) by 0 days.

(21) Appl. No.: 09/414,164

(22) Filed: Oct. 8, 1999

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTITM Computer Database 2000/05, GTI JOUVE Retrieval Software.*

* cited by examiner

*Primary Examiner*—Bruce R. Campell
*Assistant Examiner*—A Para
(74) *Attorney, Agent, or Firm*—C. A. Whealy

(57) ABSTRACT

A new distinct cultivar of Sutera plant named 'Lavender Storm', characterized by its compact, dense and prostrate or trailing plant habit; freely branching habit; numerous lavender-colored flowers; long and continuous flowering period; tolerance to high temperatures; and good garden performance.

1 Drawing Sheet

BACKGROUND OF THE INVENTION

The present invention relates to a new and distinct cultivar of Sutera plant, botanically known as *Sutera cordata*, and hereinafter referred to by the cultivar name Lavender Storm.

The new Sutera was discovered by the Inventor in Emerald, Victoria, Australia, in a seed bed of sown *Sutera cordata* seed from various random crosses of Sutera 'Mauve Mist', not patented, and the white-flowered Sutera 'Blizzard', disclosed in U.S. Plant Pat. No. 10,966. The Inventor believes that plants of the cultivar Mauve Mist served as the female parent.

Asexual reproduction of the new cultivar by terminal cuttings taken at Emerald, Victoria, Australia, has shown that the unique features of this new Sutera are stable and reproduced true to type in successive generations.

SUMMARY OF THE INVENTION

Plants of the cultivar Lavender Storm have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Lavender Storm'. These characteristics in combination distinguish 'Lavender Storm' as a new and distinct cultivar:

1. Compact, dense and prostrate or trailing plant habit.
2. Very freely branching.
3. Very floriferous.
4. Lavender-colored flowers.
5. Long and continuous flowering period, spring through fall.
6. Tolerant to high temperatures and good garden performance.

Compared to plants of the parent cultivar Mauve Mist, plants of the new Sutera are more compact; more freely flowering; tend to flow earlier; have broader petals; longer peduncles; and are more high temperature tolerant.

Compared to plants of the cultivar Lavender Showers, plants of the new Sutera have longer internodes; longer, thicker and lighter green leaves; longer, thicker and darker green petioles; shorter ped uncles; and broader flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of three typical plants of the new Sutera grown in a 25.5-cm container.

The photograph at the bottom of the sheet comprises a close-up view of a typical flowering stem of the new Sutera. Flower and foliage colors in the photograph may appear different than the actual colors due to light reflectance.

DETAILED BOTANICAL DESCRIPTION

In the following description, color references are made to The Royal Horticultural Society Colour Chart except where general terms of ordinary dictionary significance are used. Plants used for the description were grown as three per one 25.5-cm container under full sun outdoor production conditions during the spring and summer which closely approximate commercial production conditions in Bonsall, Calif. During the production of these plants, day temperatures ranged from about 21 to 35° C. and night temperatures ranged from about 13 to 18° C.

Botanical classification: *Sutera cordata* cultivar Lavender Storm.

Parentage:

*Parents.*—*Sutera cordata* cultivar Mauve Mist, not patented, and *Sutera cordata* cultivar Blizzard, disclosed in U.S. Plant Pat. No. 10,966.

Propagation:

*Type cutting.*—Terminal vegetative cuttings.

*Time to initiate roots.*—About 7 to 10 days during the summer at 22° C.

*Time to produce a rooted liner.*—About 25 to 30 days during the summer at 22° C.

*Root description.*—Numerous and fine.

Plant description:

*Crop time.*—From rooted liners, about four weeks are required to produce a fully-grown flowering plant in a 10-cm container.

*Form.*—Rounded; prostrate or trailing, compact and dense. Appropriate for 10-cm and larger containers.

*Branching habit.*—Very freely branching with multiple branches and many laterals. Usually more than 200 laterals on plants grown in larger containers.

*Plant height* (*from soil level to top of plant plane*).—About 10 cm.

*Area of spread.*—About 42 cm.

*Vigor.*—Vigorous and fast-growing.

*Lateral branches.*—Length: Primary laterals: About 27 cm. Secondary laterals: About 13 cm. Tertiary laterals: About 5.5 cm. Diameter: About 1.5 mm. Internode length: About 3.5 cm. Strength: Strong, wiry. Texture: Slightly pubescent. Color: Green, 144A, tinged with brown, 200B on upper surface.

*Foliage description.*—Leaves simple, generally symmetrical, opposite and long persisting. Quantity per lateral branch: Typically about 24 on primary lateral branches. Length: About 2 cm. Width: About 1.5 cm. Shape: Ovate. Apex: Acute. Base: Acute. Margin: Serrate. Texture: Slightly pubescent on both surfaces. Color: Young foliage, upper surface: 137A. Young foliage, lower surface: 137C. Mature foliage, upper surface: 146A. Mature foliage, lower surface: 146C. Venation, upper surface: 146C. Venation, lower surface: 146C. Petiole: Length: About 7 mm. Diameter: About 2 mm. Color: 137C.

Flower description:

*Flower type and habit.*—Single salverform flowers; sympetalous; actinomorphic; slender corolla tube abruptly flared and five-lobed. Typically two flowers per node; flowering acropetally. Flowers erect to facing outward at an acute angle. Flowers persistent.

*Flower lastingness.*—Flowers last about seven days depending on temperature and humidity.

*Natural flowering season.*—Continuously flowering under warm growing conditions.

*Quantity.*—Very freely flowering with usually about 25 to 30 open flowers per primary lateral at one time.

*Fragrance.*—Flower fragrance not detected; foliage, pungent herbaceous odor.

*Flower buds.*—Length: About 1 cm. Diameter: About 2 mm. Shape: Tubular, broader towards lobes. Color: 92C.

*Flower size.*—Diameter at lobes: About 1.4 cm. Diameter, corolla tube: About 3 mm. Overall flower height: About 1 cm.

*Corolla.*—Petal lobe length (beyond tube): About 5 mm. Petal lobe width: About 3 mm. Petal quantity: Five, fused. Petal shape: Rounded. Petal apex: Rounded. Petal margin: Entire. Texture: Smooth. Color: Petal, upper surface, when opening: 92C. Petal, lower surface, when opening: 92D. Petal, upper surface, opened flower: 92C, fading to 92D with subsequent development. Petal, lower surface, opened flower: 92D. Corolla throat: 13A.

*Calyx.*—Appearance: Narrow tube; sepals fused at base. Shape: Sepals, narrowly linear. Length: About 5 mm. Diameter: About 3 mm. Sepal quantity: Five-parted. Sepal apex: Narrowly acute. Sepal margin: Entire. Color: Upper surface: 143B. Lower surface: 143A.

*Peduncle.*—Strength: Delicate, but strong. Angle: Acute. Length: About 6 mm. Color: 144B.

*Reproductive organs.*—Stamens: Stamen number: 4. Anther shape: Reniform. Anther length: About 1 mm. Anther color: 13D. Pollen amount: Scarce. Pollen color: 13A. Pistils: Pistil length: About 8 mm. Stigma shape: Club-shaped, curled. Stigma color: 145A. Stule length: About 7 mm. Style color: 145A. Ovary color: 145A.

*Seed.*—Seed production has not been observed.

High temperature tolerance: Plants of the new Sutera have exhibited tolerance to high temperatures and have exhibited good garden performance.

Disease resistance: Resistance to pathogens common to Sutera has not been observed.

It is claimed:

1. A new and distinct cultivar of Sutera plant named 'Lavender Storm', as illustrated and described.

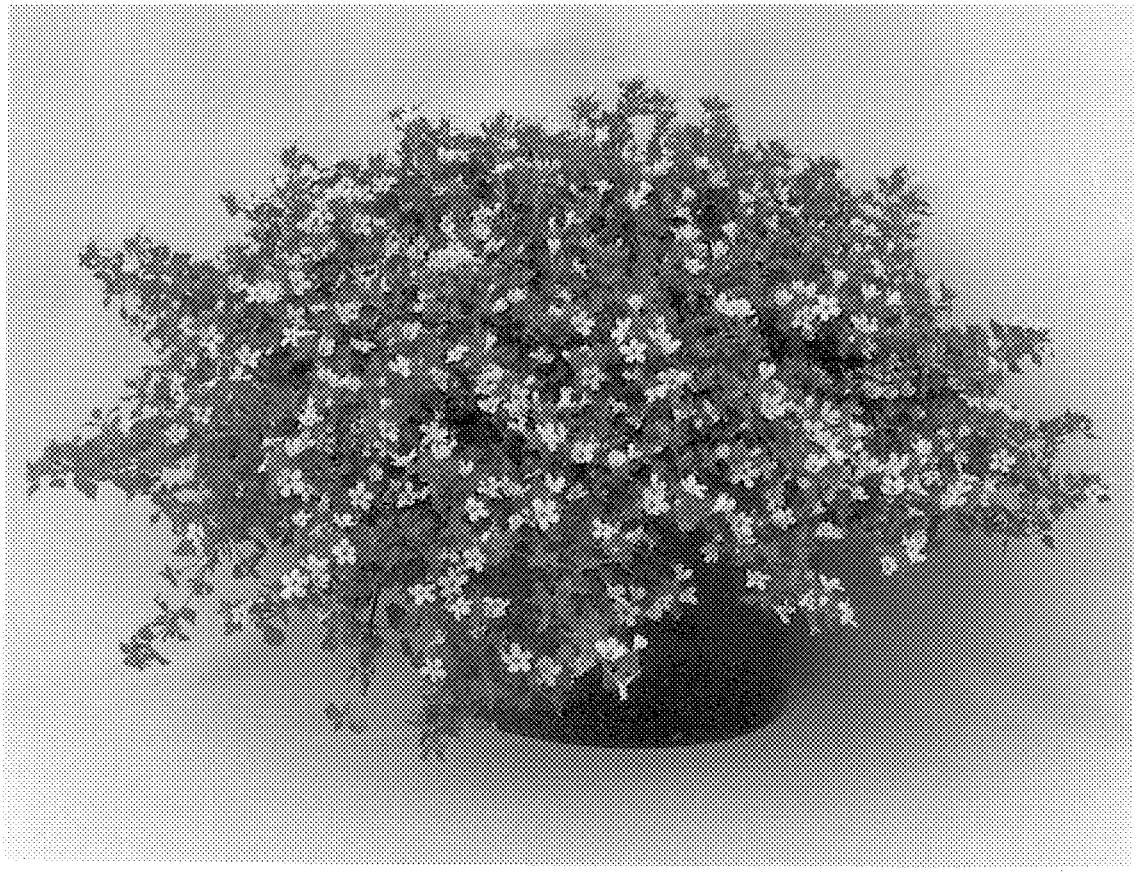
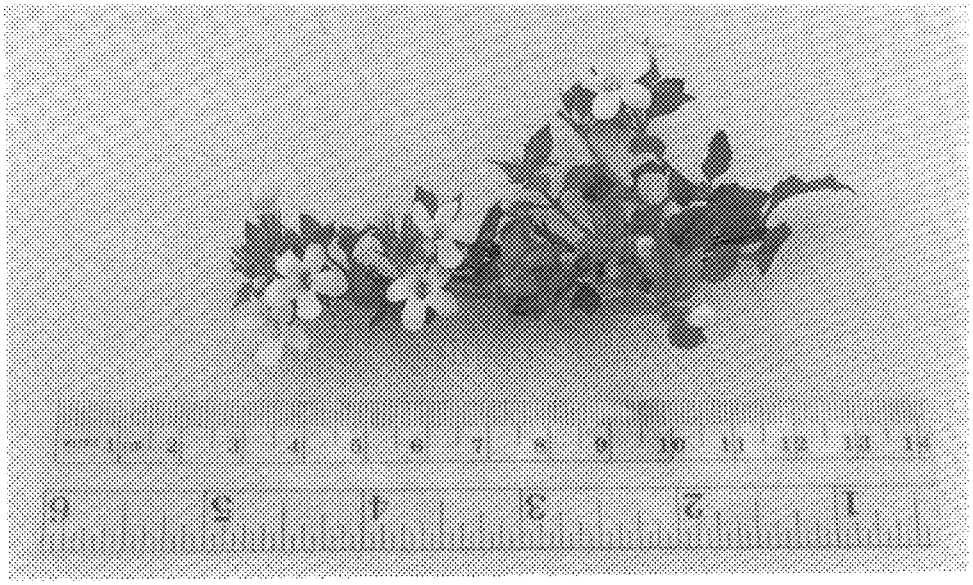

* * * * *